United States Patent
Feng

(10) Patent No.: US 7,022,349 B2
(45) Date of Patent: Apr. 4, 2006

(54) ANTIHISTAMINE COMPOSITION

(75) Inventor: Wu Wen Feng, Beijing (CN)

(73) Assignee: East West Medical Research Institute, Los Angeles, CA (US)

( * ) Notice: Subject to any disclaimer, the term of this patent is extended or adjusted under 35 U.S.C. 154(b) by 0 days.

(21) Appl. No.: 11/135,809

(22) Filed: May 24, 2005

(65) Prior Publication Data

US 2005/0220902 A1 Oct. 6, 2005

Related U.S. Application Data

(60) Division of application No. 10/692,423, filed on Oct. 23, 2003, now Pat. No. 6,896,913, which is a continuation-in-part of application No. 10/161,936, filed on Jun. 4, 2002, now abandoned.

(51) Int. Cl.
*A61K 35/78* (2006.01)
*A61K 31/35* (2006.01)
*A61K 47/00* (2006.01)

(52) U.S. Cl. ............... 424/725; 424/410; 424/439; 426/489; 426/542; 426/655; 514/27; 514/456; 536/8

(58) Field of Classification Search ........... 514/27, 514/456; 424/725, 410, 439, 440; 536/8; 426/489, 542, 655
See application file for complete search history.

(56) References Cited

U.S. PATENT DOCUMENTS

| 5,683,697 | A | 11/1997 | Tani | |
|---|---|---|---|---|
| 6,126,942 | A | 10/2000 | Yang | |
| 2003/0105027 | A1* | 6/2003 | Rosenbloom | 514/18 |
| 2003/0105031 | A1* | 6/2003 | Rosenbloom | 514/27 |

* cited by examiner

*Primary Examiner*—Herbert J. Lilling
(74) *Attorney, Agent, or Firm*—Stetina Brunda Garred & Brucker

(57) ABSTRACT

An extraction process and composition produced thereby for use as an antihistamine is disclosed. The composition comprises an extraction of *Loranthus*, which is derived from a species of *Loranthus* known to possess quantities of quercetin and avicularin, which may be administered orally in an amount up to 300 mg per day, and preferably between 100 to 300 mg per day. The extraction process comprises forming an ethanol extraction from raw *Loranthus*, filtering the extract, and passing the filtered product through a separation column, eluting, distilling and concentrating the resultant extract and thereafter applying a vacuum to remove water and solvents to produce a concentrated powdered form of the extract.

6 Claims, 1 Drawing Sheet

ANTIHISTAMINE COMPOSITION

CROSS-REFERENCE TO RELATED APPLICATIONS

The present application is a divisional application of U.S. patent application Ser. No. 10/692,423, filed Oct. 23, 2003 and issued as U.S. Pat. No. 6,896,913, which was a continuation-in-part of U.S. patent application Ser. No. 10/161,936, filed Jun. 4, 2002, now abandoned.

STATEMENT RE: FEDERALLY SPONSORED RESEARCH/DEVELOPMENT

Not Applicable

BACKGROUND OF THE INVENTION

The present invention is directed to extraction processes and compositions produced thereby that are useful as antihistamines to treat allergies and hypersensitivity reactions.

In this regard, allergic or hypersensitivity reactions and the use of antihistamines to treat the same are well-known. Generally, such a reaction is initiated by an allergen, such as a dust particle, drug, food or plant pollen, for example, that acts as an antigen to stimulate an immune response when encountered by the body. During such an event, antibodies of the immunoglobulin E(IgE) class bind with mast cells in tissues that ultimately causes histamine to be released. Typically, such allergic reactions tend to be mild and consist of primarily of watery, itchy eyes accompanied by some sneezing. Some allergic reactions, however, can be moderate to severe, and even life threatening in the case of anaphylaxis.

Most allergies are treated by the use of antihistamines, which block the histamine1 receptor. A wide variety of prescription and nonprescription antihistamines are currently available, and include promethazine, loratadine, and fexofenadine, which are available by prescription, and diphenhydramine triprolidine, and pyrilamine, which are available over the counter. Generally, such antihistamines are useful in treating allergy symptoms, and in particular seasonal hay fever, allergic rhinitis and conjunctivitis.

All such antihistamines, however, can produce undesired or adverse effects. In this regard, most antihistamines tend to cause drowsiness, and can further cause confusion, lightheadedness, dry mouth, constipation, difficulty with urination, and blurred vision. These side effects can be especially pronounced in the elderly or in individuals that have developed sensitivities to such drugs. While advances have been made to minimize some of the side effects, such as the development of nonsedating antihistamines such as loratadine and fexofenadine, the same still pose substantial risks when administered to certain individuals.

As such, there is a substantial need in the art for antihistamine compositions and methods of making the same that are therapeutically effective in treating allergic actions, as per conventional antihistamines, but do not produce many of the adverse side effects typically associated with antihistamines. There is a further need in the art for such compositions and methods for making the same that are derived from natural plant materials that can be produced via extraction processes, as opposed to conventional pharmaceutical and chemical manufacturing techniques. There is a further need in the art for such a composition and method of making of the same that are of relatively low cost, substantially easier to produce and practice, and, with respect to the antihistamine composition, are far safer and capable of being utilized in far greater patient populations than conventional antihistamine remedies.

BRIEF SUMMARY OF THE INVENTION

The present invention specifically addresses and alleviates the above-identified deficiencies in the art. In this regard, the present invention is directed to an extraction process and composition produced thereby that is safe and effective for use as an antihistamine. The composition comprises a purified extract of Loranthus selected from a species known to possess quercetin and avicularin, two well-known flavinoids in the art, that can be extracted therefrom. Exemplary of such species include Loranthus parasiticus (l.) Merr and Loranthus chinesis. The composition may be administered orally and, for human subjects, may be administered in a single daily dose of 300 mg. Preferably, such daily oral dose will be between 100 and 300 mg.

The extract is derived through a novel extraction process whereby raw flavinoid-containing Loranthus is harvested, dried and crushed such that the same preferably has a particulate size capable of passing through 40-mesh U.S. Series sieve. An ethanol solution, which is preferably 95% food grade ethanol, is added in amount of approximately five times the weight of the crushed Loranthus material to form a first admixture. The first admixture is placed within an extraction pot that is heated to no greater than 80° C. and allowed to reflux for approximately one to two hours. To further enhance the recovery of the extract, an additional amount of 95% ethanol solution may be added to the heated admixture with the resultant admixture again being reheated for up to an addition one to two hours.

The heated admixture is allowed to cool and filtered such that any residue is removed to thus produce a filtrate solution. Such filtering process is conducted until such time as the filtered solution possesses a density of 0.9 grams per cubic centimeter (g/cm3) or less and preferably between 0.8 gm/cm3 to 0.9 gm/cm3. The filtrate solution is then steam heated until the same possesses a creamy consistency and may be either dried and crushed such that the same takes the form of a powder for future use, or may be mixed with distilled water to produce the final extract. In either case, whether it be the cream derivative or powderized form thereof, the same is mixed with distilled water such that a resultant solution is produced which is approximately 15–20% by weight steam heated cream or powdered derivative thereof and 80–85% distilled water. Such solution is then passed through a filtration membrane, which is preferably 100 screen mesh, with the filtrate solution then being purified via passage through a chromatographic column utilizing XAD®-2 resin or any suitable equivalent thereof.

Once the filtrate solution is introduced into the column, distilled water is then passed through the column in an amount of approximately three times the volume of the filtrate solution (i.e., the amount introduced into the column). The distilled water is allowed to pass through the column and discarded. Following the washing of the resin with the distilled water, the column is then eluted with an ethanol solution, which is preferably approximately 50% food-grade ethanol, in an amount of approximately three to five times the volume of the column. The eluate is then collected, distilled, and concentrated until a final cream-like isolate is produced. Such isolate is then vacuum dried and crushed to a powder, which may then be packaged and then administered for use as an antihistamine.

BRIEF DESCRIPTION OF THE DRAWINGS

These as well as other features of the present invention will become more apparent upon reference to the drawings wherein.

DETAILED DESCRIPTION OF THE INVENTION

Figure 1:
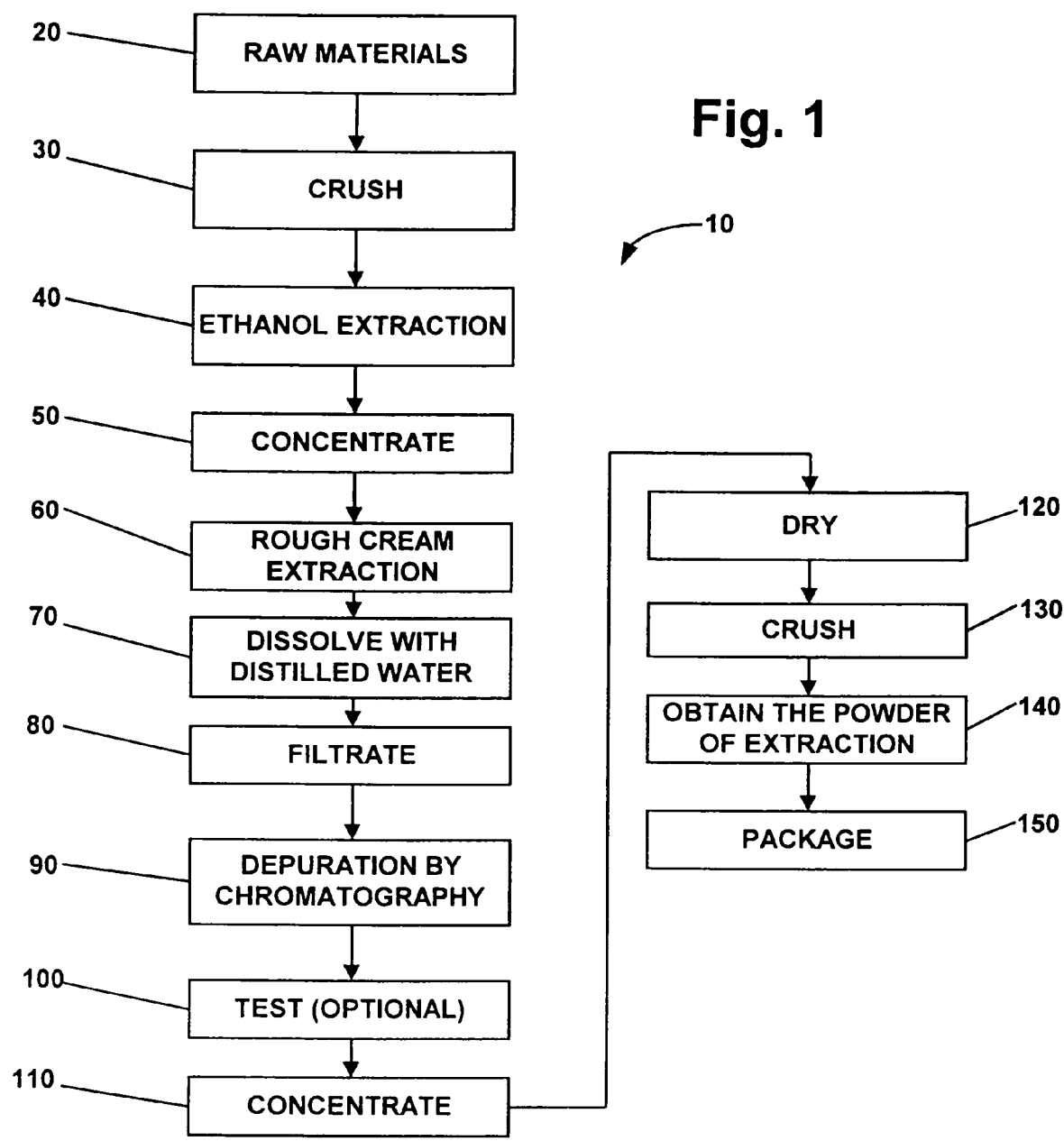
FIG. 1 is a flow chart depicting the steps to utilized to perform an extraction procedure in accordance with the preferred embodiment of the present invention.

The detailed description set forth below is intended as a description of the presently preferred embodiment of the invention, and is not intended to represent the only form in which the present invention may be constructed or utilized. The description sets forth the functions and sequences of steps for constructing and operating the invention. It is to be understood, however, that the same or equivalent functions and sequences may be accomplished by different embodiments and that they are also intended to be encompassed within the scope of the invention.

Referring now to FIG. 1, there is depicted a flow chart illustrating a process 10 for producing an extract of *Loranthus* that is useful as a safe and effective antihistamine, which has substantially fewer side effects than conventional antihistamines and further, is derived from all-natural plant products.

In the initial step 20, raw materials, namely, harvested *Loranthus* plants are provided. Although a wide variety of species of *Loranthus* are known, for purposes of practicing the present invention only those species of *Loranthus* should be utilized that are known to possess high concentrations of the flavinoids quercetin and avicularin. In preferred embodiments of the present invention, *Loranthus chinesis* and *Loranthus parasiticus* (*l.*) *Merr* plants are utilized. Such plants are well-known and are extensively planted in southern China. Such plants are typically characterized by short growing stems that are from 1–2 mm and have a diameter of typically between 0.2 to 0.8 mm. Such plants may further be characterized by leaves having a taupe to mahogany-type color. Prior to use, the materials are preferably dehydrated or otherwise dried.

Such raw materials 20 are then crushed in step 30 into particles that are preferably capable of passing through a 40-mesh US Series sieve. As is well-known, such mesh size is known in the art and are defined by the number of openings per unit area.

Once sufficiently crushed, an ethanol extraction 40 is performed whereby the crushed raw materials are mixed with a solution of approximately 95% ethanol such that the ratio of ethanol solution to crushed products is approximately 5:1 by weight. As will be appreciated by those skilled in the art, the ethanol solution will, comprise food-grade ethanol, which is commercially available from a variety, of manufacturers. The admixture of ethanol with crushed raw material is heated and allowed to reflux for approximately one to two hours at a temperature not to exceed 80° C. Preferably, such ethanol extraction is performed at approximately 78–80° C. To conduct such step, the same may be utilized in a conventional stainless steel extraction pot with reflux system. As an optional additional step, the ethanol extraction 40 may include adding additional amounts of ethanol (i.e. 95% ethanol solution) in amounts up to the original amount added; namely, approximately five times the weight of the crushed *Loranthus parasfticus* (*l.*) *Merr* and the resultant admixture again heated up to 80° C. for up to an additional two hours.

The resultant ethanol admixture is then allowed to cool and then concentrated in step 50 by filtering off any residue present in the admixture. To that end, the residue may be removed via conventional filtering techniques, such as skimming and the like, and is conducted until the solution possesses a density up to 0.9 gm/cm3 and preferably between 0.8 gm/cm3 to 0.9 gm/cm3. The removed residue may be discarded. The concentrated solution, on the other hand, is steam heated to enable the same to undergo a rough cream extraction, in next step 50. To that end, the concentrated solution is heated and steamed, preferably via the use of a jacketed kettle, until the solution transforms into a creamy residue. In this respect, such procedure may be performed via conventional ethanol extraction processes known in the art.

Once the cream has been generated through the steam heating, the same is removed and further processed via next step 60. As an alternative, the cream extracted via step 50 may be dried via conventional drying techniques, for example vacuum drying, such that the same transitions into a powder which may be stored and processed further at a later time as per the cream extracted through the rough cream extraction 50 discussed below.

In either case, whether it be the cream directly extracted from the rough cream extraction 50 or the powdered form derived therefrom, the same is dissolved with distilled water via step 60. In such step, distilled water is mixed with the cream extract or powdered form thereof such that a solution or admixture is produced which is approximately 15–20% by weight cream extract (or powder thereof) and 80–85% by weight distilled water. Once produced, the same is filtered via step 70. To that end, the solution/admixture is preferably passed through a filtration membrane, which preferably comprises a 100 screen mesh, with the filtrate being collected thereafter. Any residue not passing such screen mesh is discarded.

Such filtrate is then purified in step 80 by passing the same through a chromatography column in order to separate and isolate the sought after extract. To achieve such result, conventional chromatographic techniques may be utilized. According to a preferred embodiment, conventional chromatographic columns using XAD®-2 type media or resin may be utilized. As is well-known in the art, XAD®-2 resin produced by Rohm and Haas, of Philadelphia, Pa. is widely known and commercially available. It should be recognized, too, that any equivalent of such resin, such as Ultra-Clean™ resin produced by Restek Corporation of Bellefonte, Pa. may be utilized. Such columns with resin utilized therewith are prepared as per conventional techniques with the filtrate produced in step 70 being administered thereto as per conventional chromatographic column separation practices.

In this respect, the filtrate is administered through the top of the prepared column, followed by the passing of distilled water through the column in an amount of approximately 3 times the amount of the filtrate introduced therewithin. For example, to the extent that one liter of filtrate is administered to the column, three liters of distilled water will be passed through the column thereafter. Such distilled water is discarded once it has been passed through the chromatography column.

Following the distilled water wash of the column, the column is eluted with an approximately 50% ethanol solution of food-grade quality. Preferably, such solution is passed through the column in a volume ranging between approximately 3–5 times the volume of the chromatography column with the eluate being collected as the same is passed through the column. Once the eluate has been collected, the chromatographic column may then be rinsed with 95% ethanol solution followed by distilled water and utilized for future applications.

With respect to the ethanol eluate, the same is distilled and concentrated until a further creamy residue is isolated, as per step 110. Prior to concentrating, an optional test procedure 100 may be performed whereby the purified extract is compared against extract samples of known purity. In one preferred test, the extract is tested via thin layer chromatography wherein a portion of the extract purified in step 80 is mixed with a developing agent comprising a mix solution of chloroform, methanol and water being mixed in a ration of approximately 3:1:0.2 by weight. Preferably, such developing agent is mixed with the sample and allowed to stand for 12 hours until a bottom layer of solvent is formed. Such a bottom layer of solvent may be tested against known standards utilizing known thin layer chromatography techniques to insure sample purity and concentration.

Whether or not the same is tested for purity, the creamy residue produced in step 11 is then vacuum dried, via drying step 120, and thereafter crushed in step 130 to thus generate a powder of extraction, which is obtained in step 140. Such extraction powder may then be packaged in step 150 as per any of a variety of conventional pharmaceutical packaging techniques.

Along these lines, it is contemplated that such extraction powder may be mixed with a variety of pharmaceutically acceptable carriers and inert ingredients, such as cellulose and the like, for shipping and distribution. Additionally, such powdered form of the extract is believed to be capable of being integrated into food products, such fruit and grain based snack foods, beverages, such as fortified fruit drinks, confectioneries, candy, and the like to thus provide alternative methods of administrating such product. To the extent such extraction remains in its raw form, however, it is believed that the same should be stored away from heat sources, and also should be kept in low-humidity containers is so far as such extraction powder has been shown to readily dissolve in water. Accordingly, conventional packaging practices should be followed with respect to the storage and handling of such extraction powder.

As an illustration, two (2) non-restrictive examples of methods of practicing the extraction process of the present invention are given below.

EXAMPLE ONE

Approximately 5000 grams of *Loranthus parasiticus* (*l.*) *Merr* is crushed and placed in an extraction pot with 15 liters of a 95% ethanol solution and heated until such temperature reached 78° C. and thereafter allowed to reflux for approximately 1.5 hours. Plant residue was removed by filtration and the resultant mixture was combined with an additional ten liters of 95% ethanol solution. The resultant admixture was then heated to approximately 80° C. and allowed to reflux for approximately one hour. The ethanol solution was filtered again such that the concentrate possessed a solution density of 0.8 grams per cubic centimeter.

Such filtrate was then mixed with distilled water such that a solution was produced of approximately 20% by weight of the filtrate and 80% by weight of distilled water. Such solution was filtered and passed through a chromatography column utilizing the equivalent of XAD®-2 resin. The column was washed with five liters of distilled water and eluted thereafter with 50% ethanol. The resultant extract was collected and concentrated, via distillation, until the same became a cream isolate, which was dried further into powdered form. Such procedure generated approximately 150 grams of the *Loranthus parasiticus*(*l.*) *Merr* extract.

EXAMPLE TWO

Approximately 10 kg of *Loranthus parasiticus* (*l.*) *Merr* was crushed and placed in an extraction pot with 25 liters of 95% ethanol solution and heated to approximately 80 Nc and allowed to reflux for approximately two hours. The reflux solution was filtered and mixed with an additional 25 liters of 95% ethanol solution, which was then refluxed further at approximately 80 Nc for approximately two hours. The resultant admixture was filtered such that the concentrate possessed a density of 0.9 grams per cubic centimeter.

The filtrate was then mixed with distilled water such that a solution was produced whereby the same was approximately 15% by weight filtrate and 85% by weight distilled water. Such solution was then passed through a chromatography column utilizing a chromatographic resin equivalent to XAD®-2 followed by the administration of 10 liters of distilled water, which was passed through the chromatography column and discarded. The column was then eluted with a 50% ethanol solution, with the eluate collected and concentrated until the *Loranthus parasiticus* (*l.*) *Merr* cream extract was isolated. The same was then vacuum dried into powder form. Via such procedure, approximately 220 grams of the *Loranthus parasiticus* (*l.*) *Merr* extraction was derived.

Irrespective of the form by which the final extract produced by the foregoing process takes and is administered, the same exhibits superior properties as an antihistamine. For human subjects, it is believed that administering the powder extract derived from the process of the present invention in an amount of up to 300 mg in a single oral dose will be sufficient to treat most allergies and allergic reactions. In a preferred embodiment, a single oral dosage of approximately 100 to 300 mg in one daily oral dose it is believed sufficient to treat most allergic or hypersensitivity reactions in human subjects.

As discussed above, such oral dose may be administered via of a variety of formulations known in the art, including tablets, capsules, suspensions, or by the addition of such extract as part of a food product or beverage, such as fruit-based in grain-based snack foods, such as cereal bars and the like, fortified fruit beverages, and other fortified foods, candy and confectionaries. Advantageously, the extract of the present invention has been shown to produce little, if any, side effects typically associated with antihistamines, and further, exclusively comprises a plant derivative which omits any type of raw chemical processing as do virtually all type of antihistamines currently available.

With respect to the mode of action, it is currently believed that the *Loranthus* extract derived through the methods of the present invention contain high concentrations of flavonoids, and in particular quercetin and avicularin, which are believed to possess potent antihistamine and anti-inflammatory properties. It is further believed that such compositions possess antioxidant properties as well, and may further provide substantial therapeutic benefit in that regard. Accordingly, the process of the present invention and composition produced thereby are believed to possess substantial benefits and therapeutic properties that are readily suited to enhance health and wellness.

As will be appreciated, additional modifications and improvements of the present invention may also be apparent to those of ordinary skill in the art. Thus, the particular combination of parts and steps described and illustrated herein is intended to represent only certain embodiments of the present invention, and is not intended to serve as limitations of alternative devices and methods within the spirit and scope of the invention.

What is claimed:

1. A method for treating an allergic reaction in a human subject, said method comprising the step:
   a) administering an ethanol extract of *Loranthus* in a therapeutic amount to said human subject.

2. The method of claim 1 wherein said extract is administered orally in an amount up to 300 mg.

3. The method of claim 2 wherein said extract is administered in an amount between approximately 100 mg to 300 mg.

4. The method of claim 1 wherein said extract is administered as part of a food product.

5. The method of claim 4 wherein said food product is selected from the group consisting of fruit-based snack products, grain-based, snack products, fortified fruit drinks, fortified dairy products, candy and confectionaries.

6. The method of claim 1 wherein said extract of *Loranthus* is derived from a species of *Loranthus* selected from the group consisting of *Loranthus parasiticus* (*l.*) *Merr* and *Loranthus chinesis*.

* * * * *